(12) United States Patent
Philot et al.

(10) Patent No.: US 6,238,358 B1
(45) Date of Patent: May 29, 2001

(54) COMBINED RECONFIGURABLE MULTI-PURPOSE EXTERNAL ORTHOPEDIC FIXATION DEVICE AND MULTI-FUNCTIONAL REHABILITATIVE PROSTHESIS

(76) Inventors: George Guarany Philot; Gisleine Martin Philot, both of Rua Diogo Alvares, 1074 - casa 61, 06700-000- Cotia- SP (BR)

( * ) Notice: Subject to any disclaimer, the term of this patent is extended or adjusted under 35 U.S.C. 154(b) by 0 days.

(21) Appl. No.: 09/147,859
(22) PCT Filed: Jul. 18, 1997
(86) PCT No.: PCT/BR97/00033
  § 371 Date: Mar. 16, 1999
  § 102(e) Date: Mar. 16, 1999
(87) PCT Pub. No.: WO99/03432
  PCT Pub. Date: Jan. 28, 1999
(51) Int. Cl.⁷ .................................................. A61F 5/00
(52) U.S. Cl. .................................... 602/5; 602/20; 602/21
(58) Field of Search .............................. 602/22, 5, 16, 602/20–21, 30; 128/878, 879

(56) References Cited

U.S. PATENT DOCUMENTS

| 3,620,211 | 11/1971 | Goodell et al. | 128/89 |
| 4,243,026 | 1/1981 | Barber | 128/77 |
| 4,672,954 | 6/1987 | Panzer | 128/79 |
| 5,324,251 | * 6/1994 | Watson | 602/16 |

FOREIGN PATENT DOCUMENTS

| 824483 | 2/1938 | (FR) . |
| 110377 | 11/1971 | (GB) . |

* cited by examiner

Primary Examiner—Michael A. Brown
Assistant Examiner—Lalita M. Hamilton
(74) Attorney, Agent, or Firm—Abelman, Frayne & Schwab

(57) ABSTRACT

A combined, reconfigurable, multi-purpose external orthopedic fixation device and multi-functional prosthesis, for use alternatively as an external orthopedic fixation device for providing support and/or traction for a sprained, fractured, or broken limb of a warm-blooded animal, especially a human being, and as an artificial prosthesis for providing both substitute elementary limb functionality and substitute multi-purpose specific task functionality of a limb, especially an upper limb, such as a finger, hand, wrist, forearm, or elbow, of a warm-blooded animal, especially a human being, is disclosed. The apparatus includes at least one flexible tubular elongate member having a flexible strengthening rod therein, and a pair of end caps. Other embodiments of the apparatus further include one or a plurality of one or more additional elements including a cushioning support that is slidable along the elongate member; a stop for fixing the position of a cushioning support; a uni-dimensional joint for connecting ends of one or more elongate members together in a two-dimensional configuration; a two-dimensional joint for connecting ends of two or more elongate members together in a three-dimensional configuration; a panel of webbing material for supporting a limb; a rigid support member generally contoured to and for supporting a specific limb; and a variety of implements for performing certain useful functions, such as personal hygiene and grooming, eating, writing, and simple chores, that can be attached to one or more ends of an elongate member in place of the end caps.

53 Claims, 14 Drawing Sheets

FIG. 1
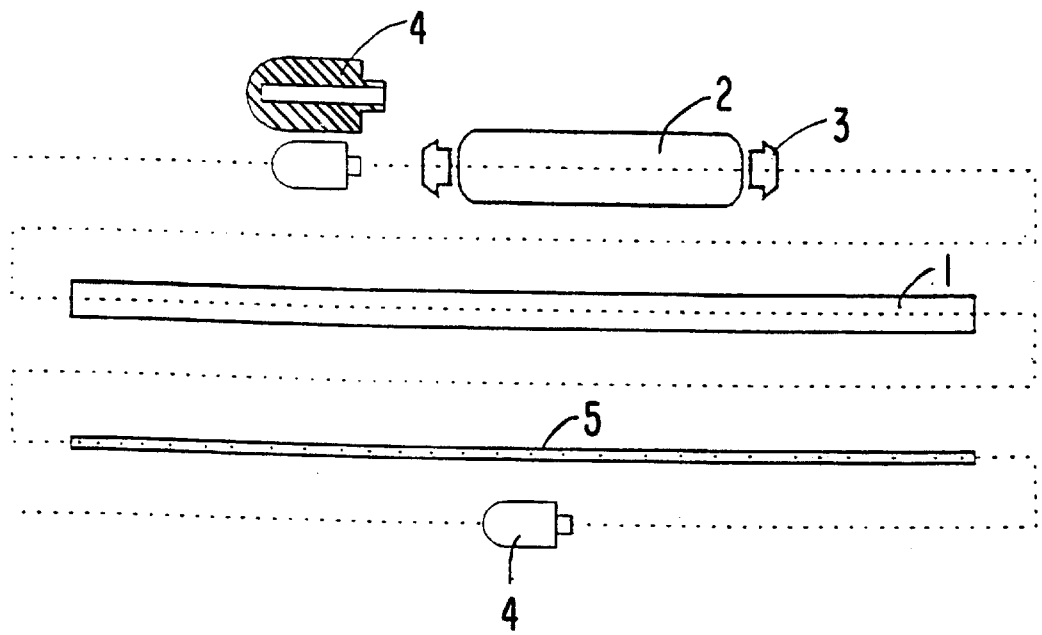
FIG. 2a
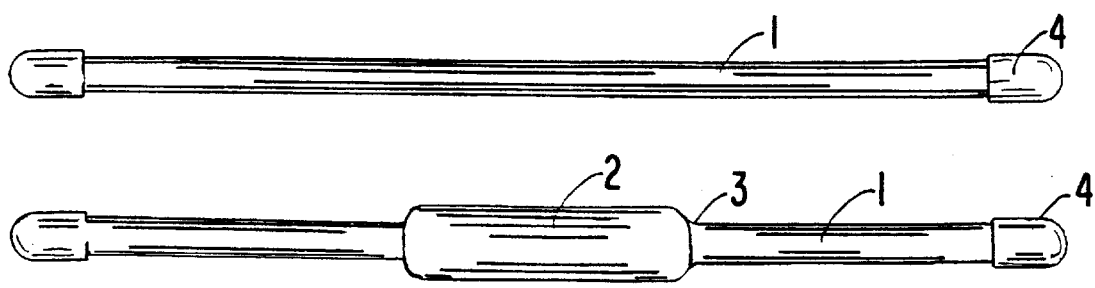
FIG. 2b

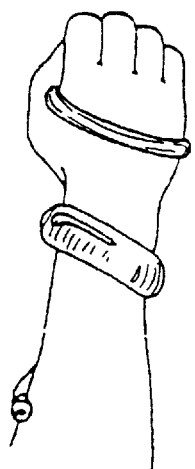
FIG. 9a
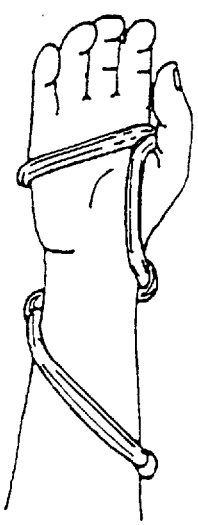
FIG. 9b
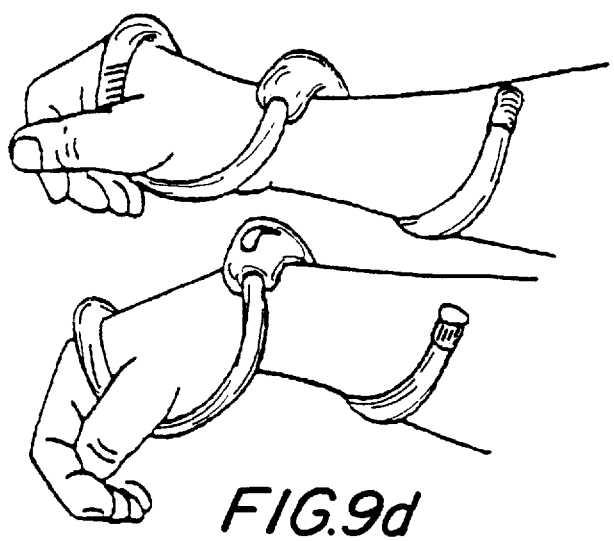
FIG. 9c
FIG. 9d
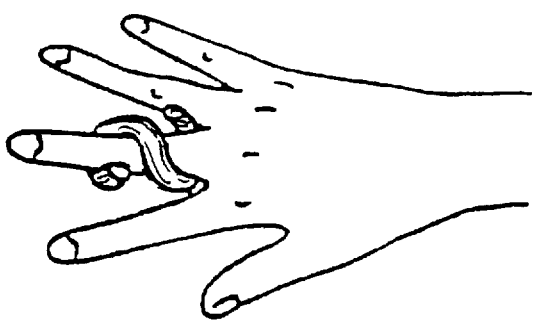
FIG. 10
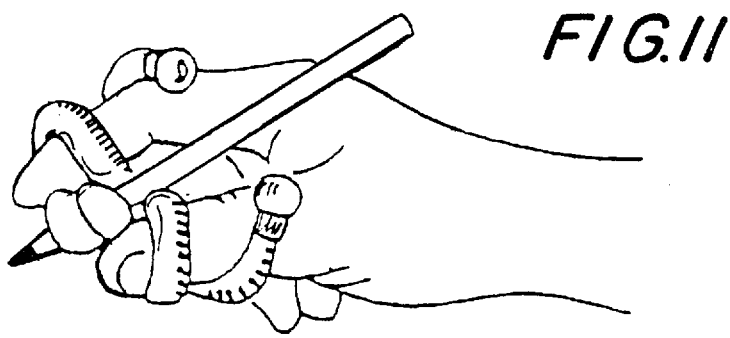
FIG. 11

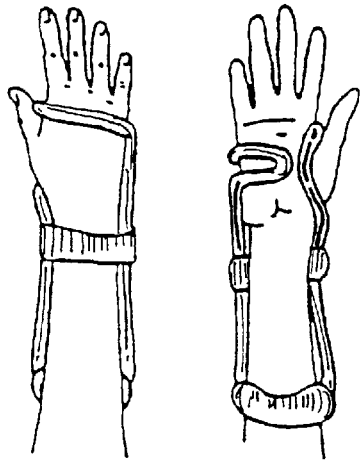 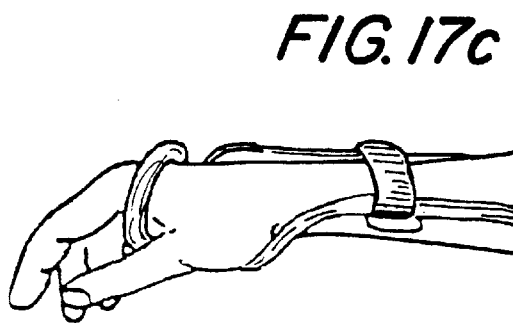
FIG.17a  FIG.17b  FIG.17c
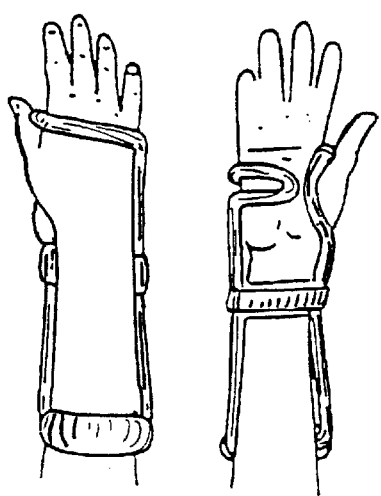 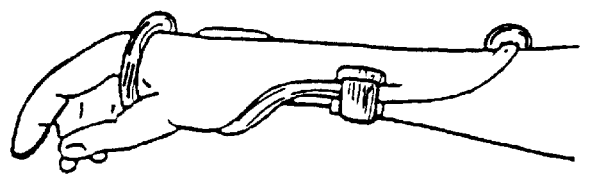 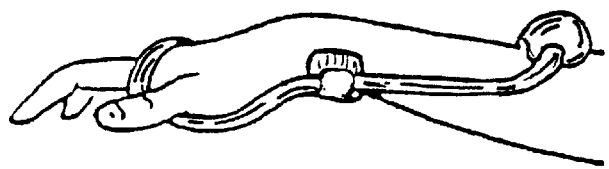
FIG.18a  FIG.18b  FIG.18c
FIG.18d

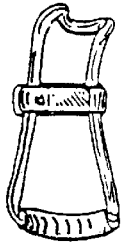 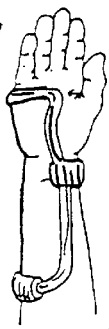 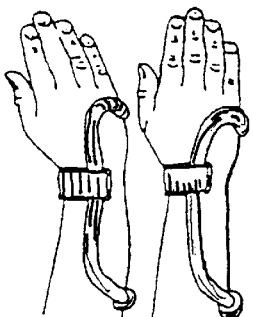
FIG.19a  FIG.19b  FIG.19c  FIG.19d
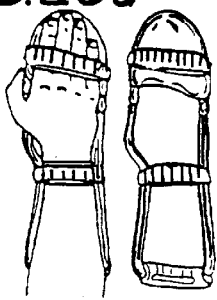
FIG.20a  FIG.20b

FIG.21a

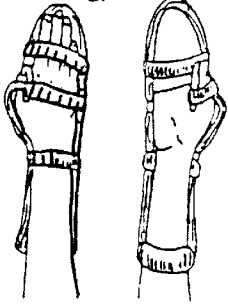
FIG.22a  FIG.22b

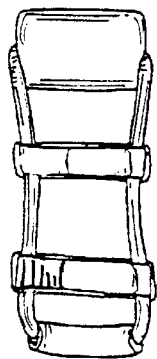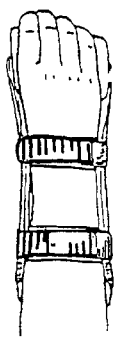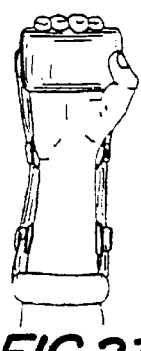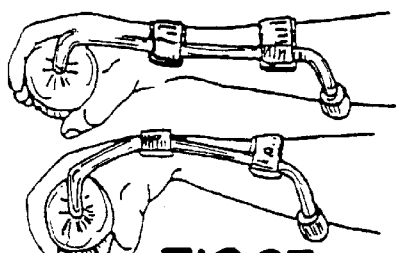
FIG.23a  FIG.23b  FIG.23c  FIG.23d  FIG.23e
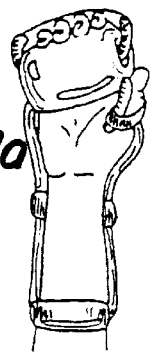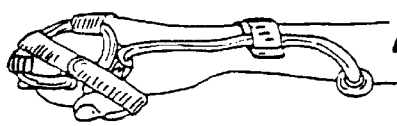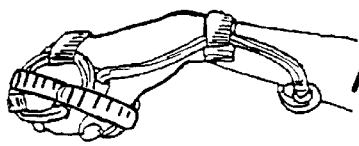
FIG.24a  FIG.24b  FIG.24c
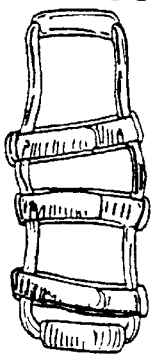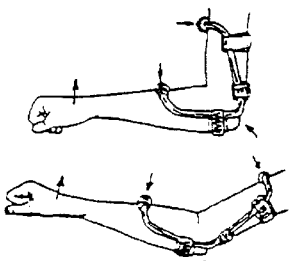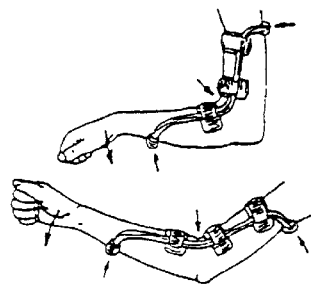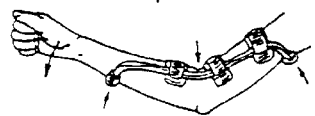
FIG.25a  FIG.25b  FIG.25c  FIG.25d  FIG.25e

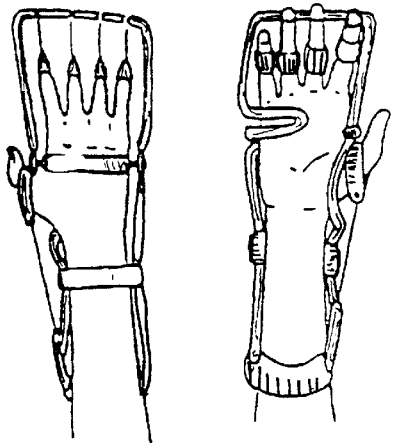
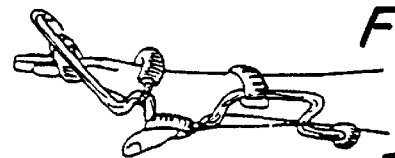
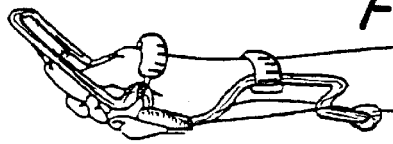
FIG.26a  FIG.26b  FIG.26c  FIG.26d  FIG.26e
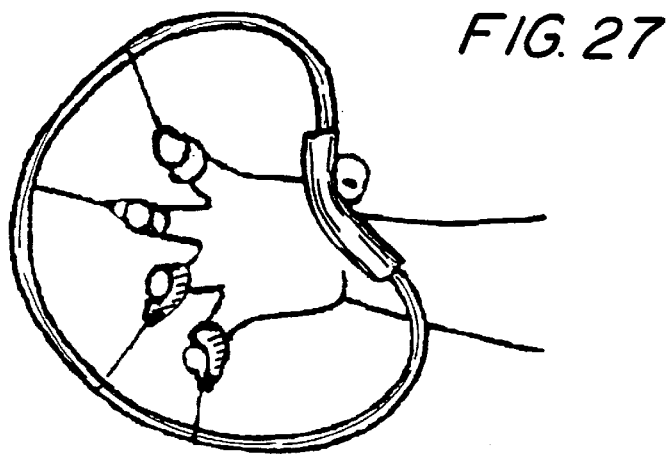
FIG. 27

FIG. 28
FIG. 29
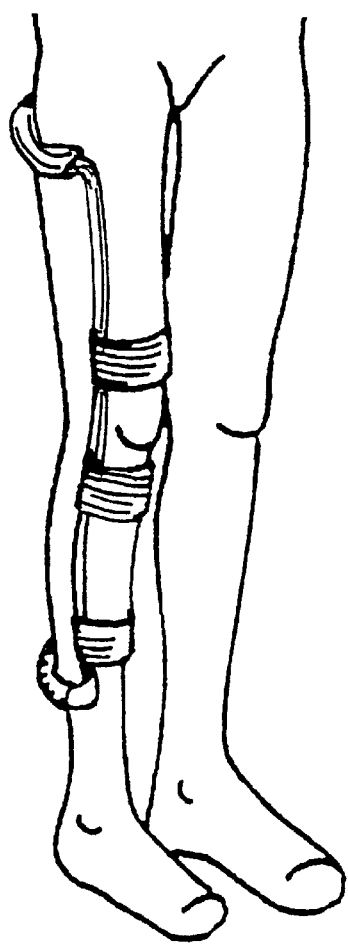
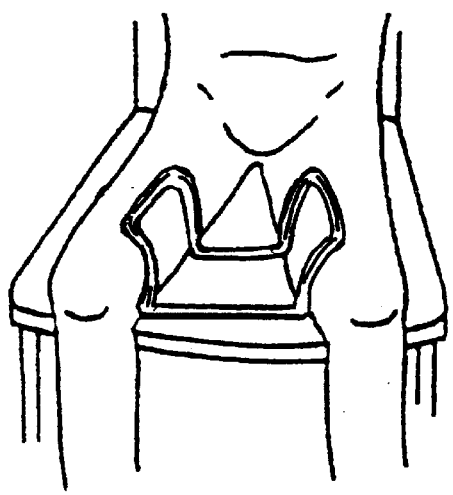
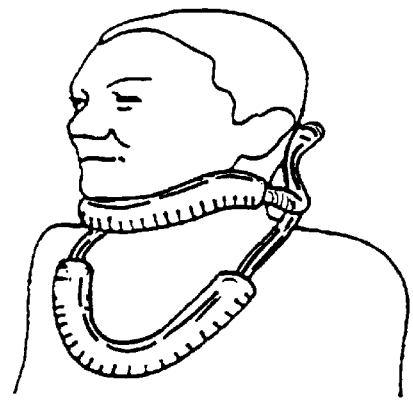
FIG. 30

COMBINED RECONFIGURABLE MULTI-PURPOSE EXTERNAL ORTHOPEDIC FIXATION DEVICE AND MULTI-FUNCTIONAL REHABILITATIVE PROSTHESIS

FIELD OF INVENTION

The present invention concerns a new moldable therapeutic orthopedic fitting device for orthopedic and/or neurological patients. This device is an orthesis which has the main purpose to aid, to support, to put in position, to protect, to correct, to reeducate, to prevent, to ease and/or to substitute certain functions of the human body, mainly the upper limbs.

The new moldable therapeutic orthopedic fitting device of the present invention enables the therapeutic positioning, to fit the upper limbs: neck, trunk and the lower limbs. The device of the present invention has flexible characteristics and can undergo any changes that may become necessary in a simple and practical form.

In addition, the new moldable therapeutic orthopedic fitting device of the present invention is specially suitable for the therapeutic positioning of the upper limbs such as the hands, the fingers and forearm for all kinds of lesions. The device of the present invention is capable of replacing previously known devices, while simultaneously representing an advancement in the field of orthesis such as splints, vests and collars. This device enables the initial therapeutic positioning which can be changed in accordance with the progress or regression of the pathological condition, or act as an important preventative agent. The device of the present invention is also capable of providing substitute function for the grasp of the hand.

BACKGROUND OF THE INVENTION

Several techniques have been developed throughout the history of orthopedics and neurology as forms of intercession which would be efficient for the handicapped individual.

The most common technique employed was the manufacturing of thickened cables generally made out of wood, rubber, foam and plastic materials, fastened with a strip of leather, fabric or Velcro which are placed on, as example cutlery, pencils, wax chalk and razors. However such a adaptation is an impediment to the release of the feeble grasp or the associated reactions modifying the tonus of the muscles which is specially common in groups of patients such as they having cerebral palsy, AVC sequel, skull trauma sequel etc. Besides, quite often these devices are attached to the injured hands and in these cases it is impossible to avoid an unnatural and uncomfortable positioning of the hands.

Velcro and leather bandages are also used. In addition, splints made from heat molded materials which require a lot of handling in order to manufacture the orthesis, have also been previously used. These thermoplastic devices cover completely the palm and the back of the hand which can produce a rather unaesthetic effect and quite often produce chafing and scars in the abradable regions of the hand and obstruct the use of the sense of touch and cognitive recollection. Further they may cause swellings and discomfort due to sweating.

Seriously handicapped individuals as those with cerebral palsy spastics, dystonics, choreics, athetoids, spinal tetraplegics, patients with muscular dystrophy, demyelination, malformed, serious burns, rheumatoid arthritis, Parkinson's disease, etc., are totally incapacitated in the use of their hands, especially when exhibiting motor uncontrollability of the entire upper limb.

The most common technique to manufacture these types of devices requires appropriate measurements of the affected limb, development of drawings on paper, development of plaster cast of the compromised limb which can be quite painful some times, improvements on casting the plaster, removing the cast, fabricating the splint of aluminum, leather, neoprene or similar, providing the device with catches, washers, strings, or Velcro and, after this, carrying out many tests with the device. Usually, there is a need for several steps and the use of many elements to obtain a final product which has a rigid structure being specific for each individual. As these devices are produced during a specific pathological moment, any changes in the clinical status as well as any ergonomic alteration, as to weight (loss or gain), or as to size (in case of children and adolescents), shall make the orthesis incompatible with the new sizes thereby requiring the manufacture of a new orthesis.

Another plastic deformation technique can be used to produce some models for specific pathologies providing with the scaling of measurements to adapt themselves to the normal parametrs of a specific population group. However this technique will not allow for any ergonomic or anatomic adjustment. Also this technique causes a great deal of discomfort since this is not endowed with any system of ventilation and usually covers large areas of the affected limb or articulation.

An improved technology is the low temperature thermo-molding of plastic sheets which requires extremely accurate measurements and manufacturing of a paper mold, cutting, heating and application of the still hot product on the affected limb. After this the device is cured and finished by grinding the edges, installing the structural supports and the Velcro. In some cases it will be necessary to apply inside the vest, collar or splint a protective film or cushioning layer in view of the hardness of the material and also to avoid problems on the skin and with ergonomic development of the individual. As the first mentioned technique is specific for each case and for each different individual and given the nature of the thermo-molding material, it undergoes changes within approximately eight month and it will become brittle.

Another technology is disclosed in U.S. Pat. No. 4,617,921 and refers to an immobilizing structure consisting of a flexible compartment which contains internally a set of rods (called die material) and a thermoplastic product which envelopes the aforementioned rods and imparts shape to the structure depending of its physical state (whether solid or liquid), that is, depending on its temperature. As this device has a complex structure, a rigorous control is required for heating by both the manufacturer and the therapist who must be thoroughly trained in this technology in order not to cause any burns to the limb under treatment. In order to avoid the usual ordinary oscillations of temperatures in the work place, or even during a shower, the internal rods and its shapes (braided, twisted, etc.) must be carefully chosen. The thermoplastic material must be able to resist the repeated heating and cooling cycles and it must have an excellent thermal conductivity whereas the external compartment must be expansion proof. To produce this device, heating and cooling sources are needed. Therefore it requires an accurate monitoring of the temperature of said structure in order to guarantee the patient's safety.

Therefore, there is no means, until now, useful as an adapter or special device for the upper limbs that provides for any kind of independence without the help of a third party in order to be able to scribble or to paint on a sheet of paper, to write, to point a finger to a figure or an object, and/or to grasp anything.

BRIEF DESCRIPTION OF INVENTION

The objective of the present invention is to provide a device for therapeutic use which does not present the above mentioned inconveniences and that it be efficient in its application.

Another objective of the present invention is to provide a device for therapeutic applications comprising means for supporting and attachment, fast and easy means for fitting and refitting and for the interchange of accessories, besides being able to position efficiently the forearm and the hand by preserving the sensory contact and also to provide the chance for the use of the remaining muscular system, if any.

The device of the present invention is quite pleasant from an esthetic stand point. It prevents deformities and while a therapeutic it can be used to provide more natural grasps. It also inhibits associated reactions which in the course of the years may cause damage to individuals who have neurological lesions, and in many cases is a help in facilitating either thick, medium or thin grasps. It can also be used as an exerciser for flexing and extending the fingers when coupled to elastic means. In the case of individuals without any hand functions, the device of the invention can provide substitute functionality when coupled to forks, spoons, knives, combs, hair and paint brushes, pens and any other utensils. Besides being a rest or dynamic orthesis they are also, exercisers, and orthopedic immobilization splints.

The device of the present invention introduces the facility to change at any needed moment its initial ergonomy by adjusting itself to unexpected or to temporary handicapped situations or circumstances, or simply to the evolutionary stage of incapacity. It is of light weight, respecting the sensitive areas, since it covers only a small part of the limb because its original tubular shape, with respect to the points of physical support. By covering a few areas and by adequately distributing the forces of tension and pressure, the device of the invention preserves the body's natural image by not hiding a specific part of the body as it is the case with the prior technology for thermo-molding materials. Thus it allows for greater ventilation of the limb by allowing the natural breathing of the individual's skin.

The present invention has concepts which are not to be found in any of the currently known technologies since it enables the initial shape of the device to be changed whenever it becomes necessary to adjust it to each individual's ergonomic and anatomic aspect. It is practical and does not require any heating or cooling control: it is recyclable, adjustable, flexible, fitting and capable of being reconfigured or refitted. It is adaptable to a particular stage in each individual's given pathology.

The device of the present invention with the precision characteristics and fittings presented herewith reveal many extraordinary advantages in the field of rehabilitation.

The technologies of the state of the art employ materials with thermo-molding or deformation characteristics lending themselves to assume several shapes which are suitable for different applications. However, they are neither re-adjustable nor flexible or suitable for the thermo-molding of intermediary and peculiar evolutionary processes. For each new application or clinical stage manufacturing of another device is required.

BRIEF DESCRIPTION OF DRAWINGS

FIG. 1 is an exploded side view of one embodiment of the medical device according to the present invention, with "terminal" end caps.

FIGS. 2a, b show side views of embodiments of the medical device according to the present invention with end caps, and without and with a cushioning support, respectively.

FIGS. 9a, b, c and d show different views of the embodiment of the medical device according to the present invention, fitted with terminal connectors for attaching functional implements, with the device being used to provide orthopedic fixation and support, while still enabling flexure.

FIG. 10 shows one embodiment of the medical device according to the present invention FIG. 11 shows an embodiment of the medical device according to the present invention configured to provide substitute functionality by holding a writing implement while providing fixation and support to at least several fingers on the hand.

FIGS. 17a–c show different views of an embodiment of the medical device of the present invention configured as an orthopedic fixation device for holding the wrist and lower arm in traction.

FIGS. 18a–d show different views of an alternative configuration and placement of the medical device of FIGS. 17a–c.

FIGS. 19a–d show different views of another alternative embodiment of the medical device of the present invention, configured as an orthopedic fixation device for the lower arm, wrist, and hand.

FIGS. 21a–c show different views of yet another alternative embodiment of the medical device according to the present invention, configured as an orthopedic fixation device for the lower arm, wrist, and hand.

FIGS. 22a–d show different views of still yet another alternative embodiment of the medical device according to the present invention, configured as an orthopedic fixation device for the lower arm, wrist, and hand.

FIGS. 23a–e show different views of an embodiment of the medical device according to present invention configured as an orthopedic fixation device for the lower arm, wrist, and hand, with a cushioning support for the hand and a plurality of attachment straps, and showing the enablement of flexion of the hand and fingers.

FIGS. 24a–c show different views of an alternative form of attachment of the orthopedic fixation medical device according to FIGS. 23a–e.

FIGS. 25a–e show different views of an embodiment of an embodiment of the medical device according to the present invention configured as an orthopedic fixation device for providing traction to the elbow while still enabling flexion thereof.

FIGS. 26a–e show different views of alternative embodiments (a and b) of the medical device according to the present invention configured as an orthopedic fixation device for providing traction individually to the main four fingers of the hand, while still permitting flexion of those fingers collectively from the base of the fingers and also enabling flexion of the non-tractioned thumb.

FIG. 27 shows an embodiment of the medical device according to the present invention configured as an orthopedic fixation device for providing traction to the hand and fingers.

FIG. 28 shows an embodiment of the medical device according to the present invention configured as an orthopedic fixation device for a leg.

FIG. 29 shows an embodiment of the medical device according to the present invention configured as an orthopedic support and separator for the pelvic region.

FIG. 30 shows an embodiment of the medical device according to the present invention configured as an orthopedic support for the neck.

DETAILED DESCRIPTION OF INVENTION

Figure 3:
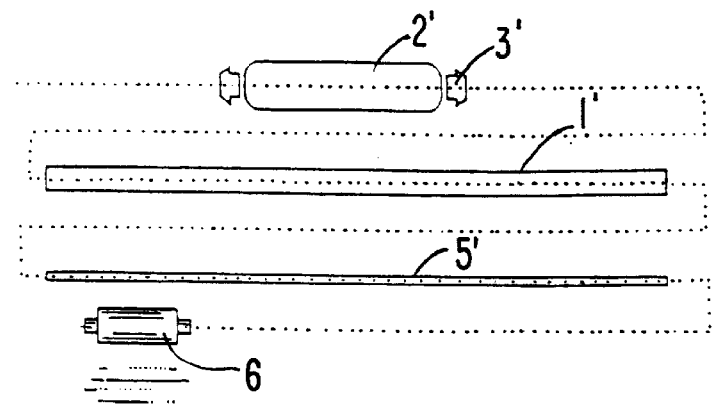
FIG. 3 is an exploded side view of another embodiment of the medical device according to the present invention, with a joint for connecting the tubular member of the device to itself or to other tubular members.

According to FIGS. 1 and 2 the device of the present invention comprises a flexible cable (1) provided with one or more soft supports (2) which are stabilized through their backstops (3) with two opposite terminals (4). One of these terminals (4) can be used as receptor terminal for any one of the accessories.

The flexible cable (1) comprises a tube (1') of flexible material with circular cross section in which is inserted a flexible metal rod (5) with knurled ends for the pressure attachment of the circular cross section terminals (4).

Figure 4A:
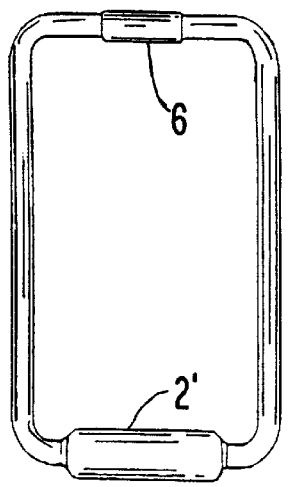
FIGS. 4a, b show the embodiment of FIG. 3 in a closed loop configuration using the connecting joint to constitute one form of orthopedic fixation device frame.
Figure 4B:
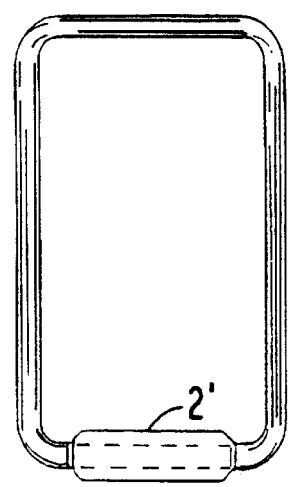
Figure 5A:
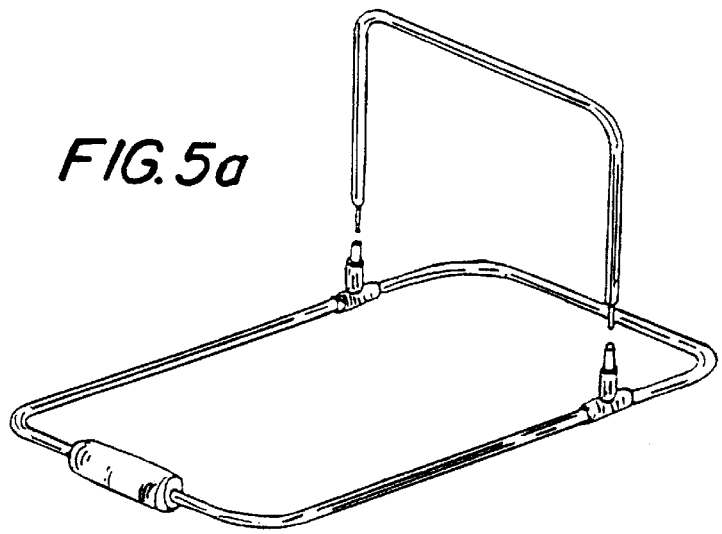
FIGS. 5a, b show another embodiment of the medical device according to the present invention, including a plurality of tubular members and a plurality of "T" connection joints, assembled as a more complex orthopedic fixation device frame.
Figure 5B:
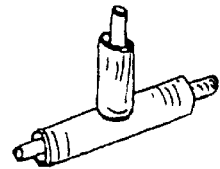
Figure 6A:
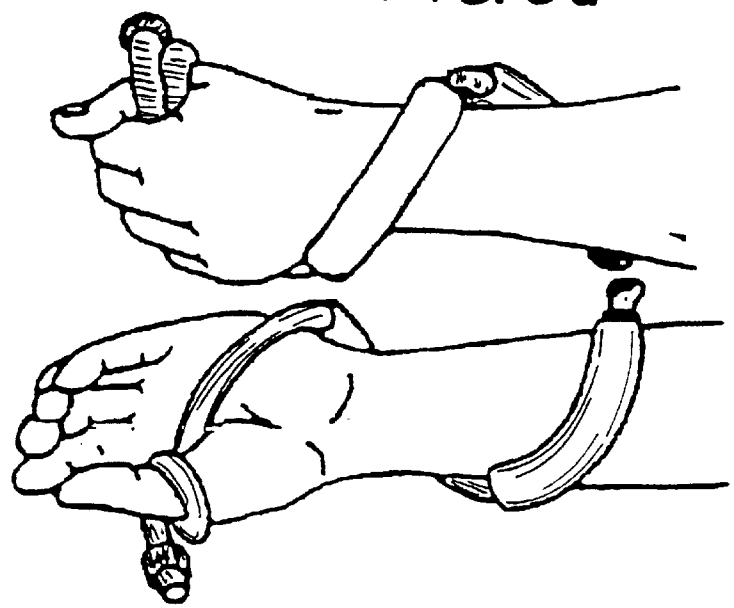
FIGS. 6a, b, and c show different views of one embodiment of the medical device according to the present invention, configured as a manual prosthetic device and fitted with terminal connectors for attaching funtional implements.
Figure 6B:
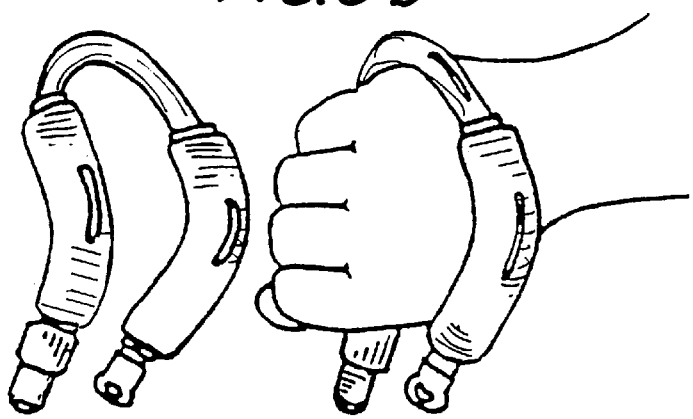
Figure 6C:
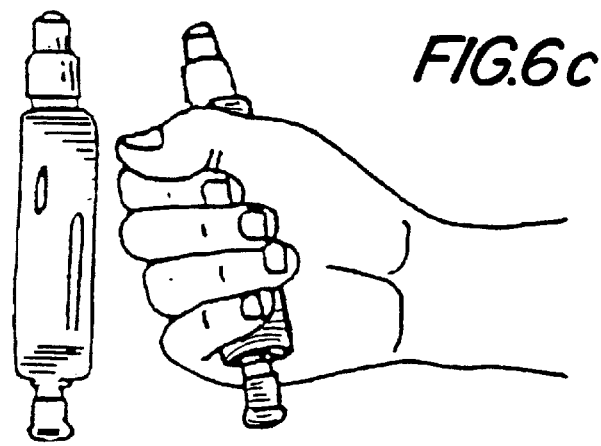
Figures 7A, 7B, 7C:
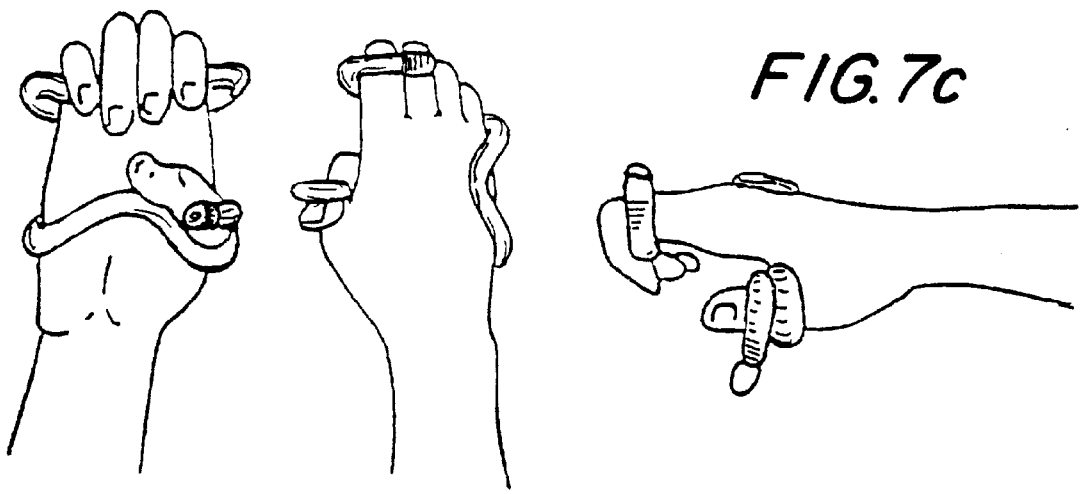
FIGS. 7a, b, and c show different views of one embodiment of the medical device according to the present invention, configured as an orthopedic fixation device for the hand and fingers.
Figure 8A:
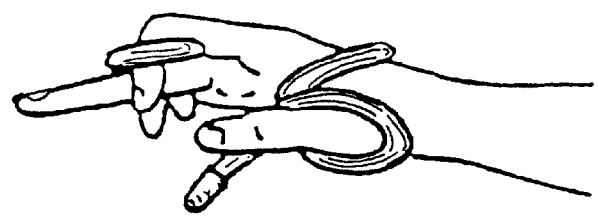
FIGS. 8a, b show different views of one embodiment of the medical device according to the present invention, fitted with at least one terminal connector for attaching functional implements, with the device being configured as an orthopedic fixation device and also to provide substitute functionality.
Figure 8B:
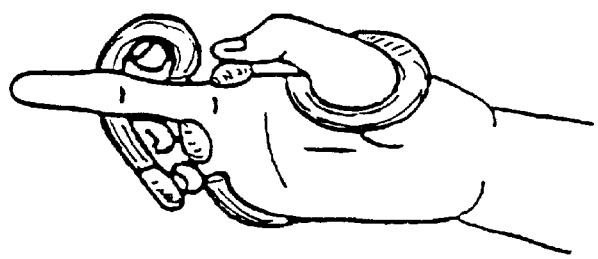
Figure 12:
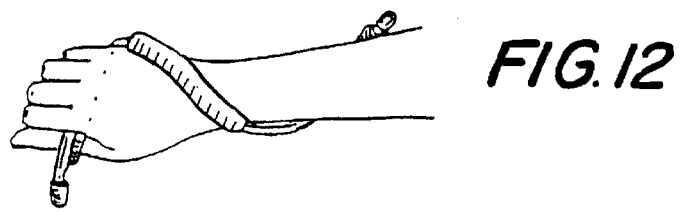
FIG. 12 shows an embodiment of the medical device according to the present invention with end connectors for attaching implements, with the device shown in a position for use as an artificial prosthesis for providing substitute functionality.
Figure 13:
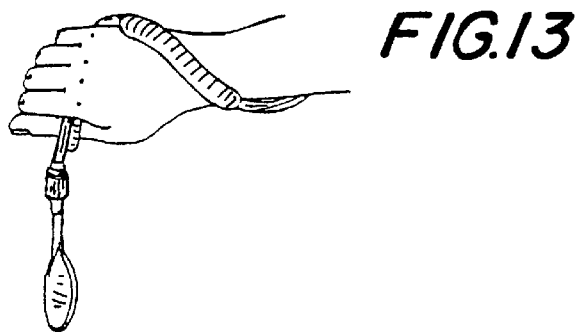
FIG. 13 shows the device of FIG. 12 with an implement attached to one of the end connectors.
Figure 14:
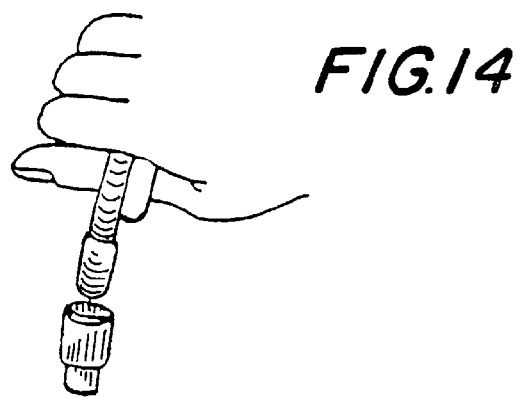
FIG. 14 shows a detailed view of the attachment of an implement to an end connector.
Figure 15:
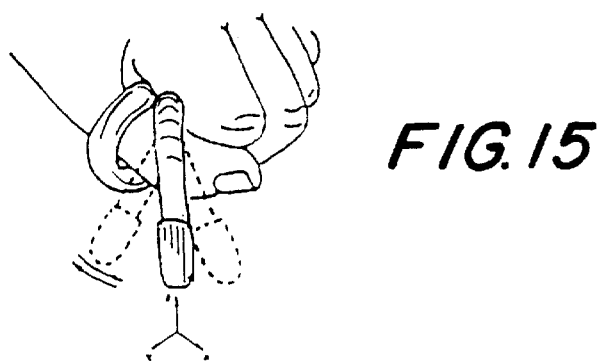
FIG. 15 shows the three-dimensional flexibility along x-y-z axes, of an embodiment of the medical device according to the present invention configured as an artificial prosthesis for providing substitute functionality.

As shown in the FIGS. 3 and 4, the device of the present invention comprises the same elements of FIGS. 1 and 2, although in this proposal we have substituted the terminals (4) of FIGS. 1 and 2 by a cross sectional circular joint (6) which will attach by pressure to the knurled ends of the metal rod (5'). Usually the joint (6) is covered with a soft support (2') duly stabilized by its backstops (3'). In this embodiment with a joint (6) more than one soft supports can be used in order to ensure a greater contact and comfort of the affected body part.

It should be noted that flexible cable (1) and (1') and supports (2) and (2') have the purpose to comfortably fasten the device to the affected part of the body as well as to provide the necessary angle for a better posturing. Thus, the prior aforementioned molding and remolding techniques are characteristics of the device, which enables through its flexibility, the wrapping of the affected portion of the body as well as modification of its shape, and the provision of support and functional utility, as needed.

The interchange of terminals and accessories interchange has the purpose to accommodating as many instruments, tools and utensils as necessary for the user's daily activities.

FIG. 16 shows a non-limiting variety of various functional implements that are attachable to an embodiment of the medical device according to the present invention that is provided with end connectors.

Figure 16A:
FIGS. 16a–o show various functional implements that are attachable to a medical device according to the present invention that is configured for use as an artificial prosthesis for providing substitute functionality and that is provided with terminal connectors for the attachment of the implements.
Figure 16B:
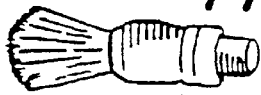
Figure 16C:
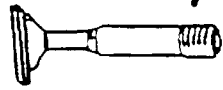
Figure 16D:
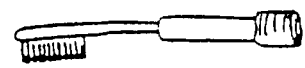
Figure 16E:
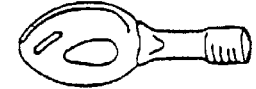
Figure 16F:
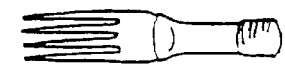
Figure 16G:
Figure 16H:
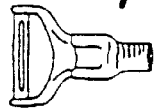
Figure 16I:
Figure 16J:
Figure 16K:
Figure 16L:
Figure 16M:
Figure 16N:
Figure 16O:
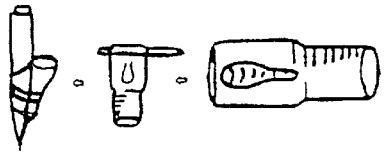
Figure 20C:
FIGS. 20a–d show different views of another alternative embodiment of the medical device according to the present invention, configured as an orthopedic fixation device for the lower arm, wrist, and hand, showing the range of motion and flexion of the hand and fingers permitted while the device is being worn.
Figure 20D:
Figure 20E:
Figure 20F:
Figure 21B:
Figure 21C:
Figure 22C:
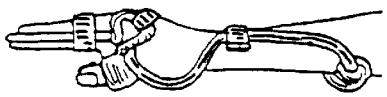
Figure 22D:
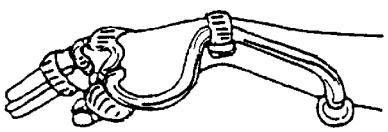
Figure 31:
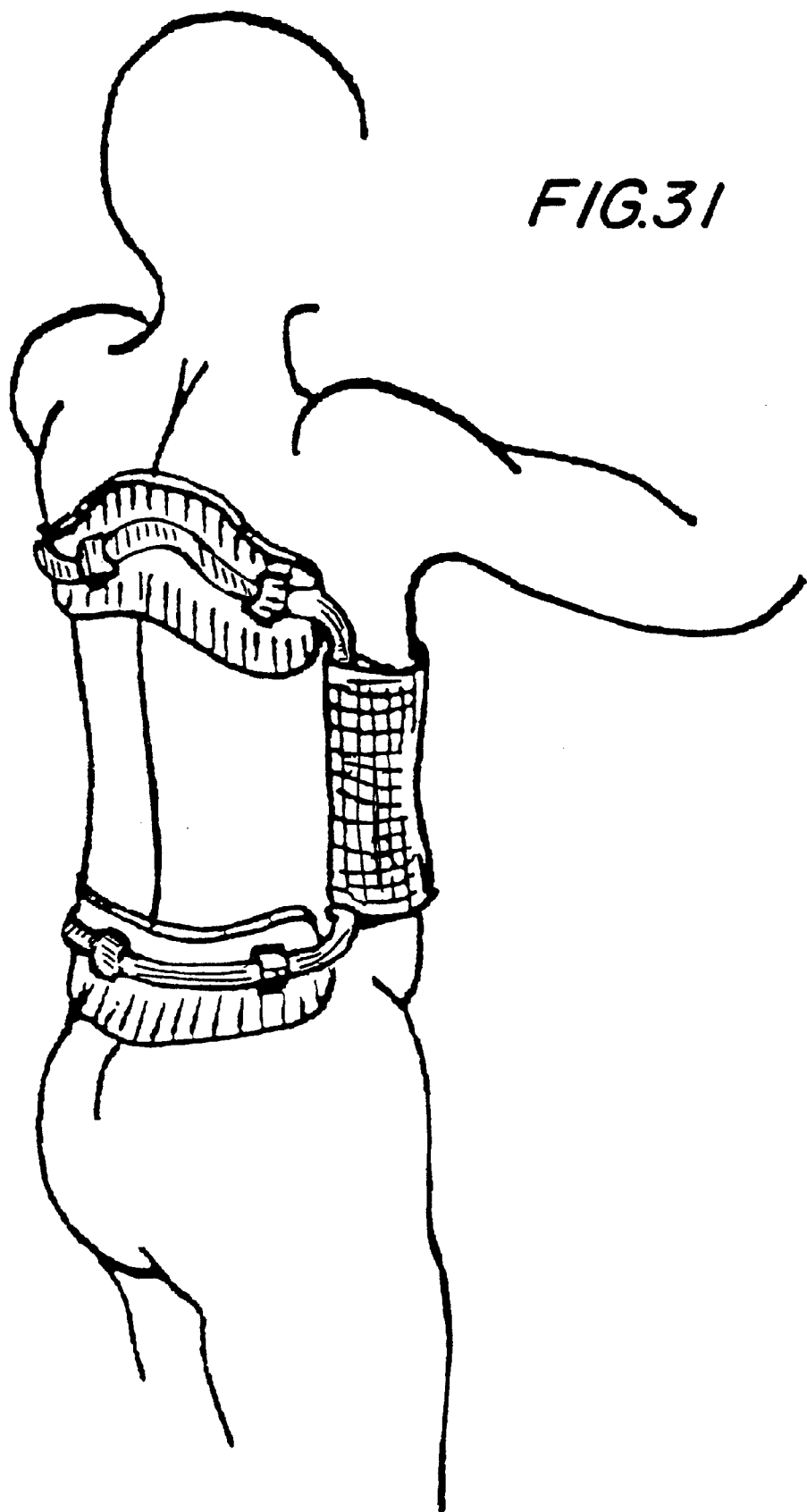
FIG. 31 shows an embodiment of the medical device according to the present invention configured as an orthopedic support for the back.
Figure 32:
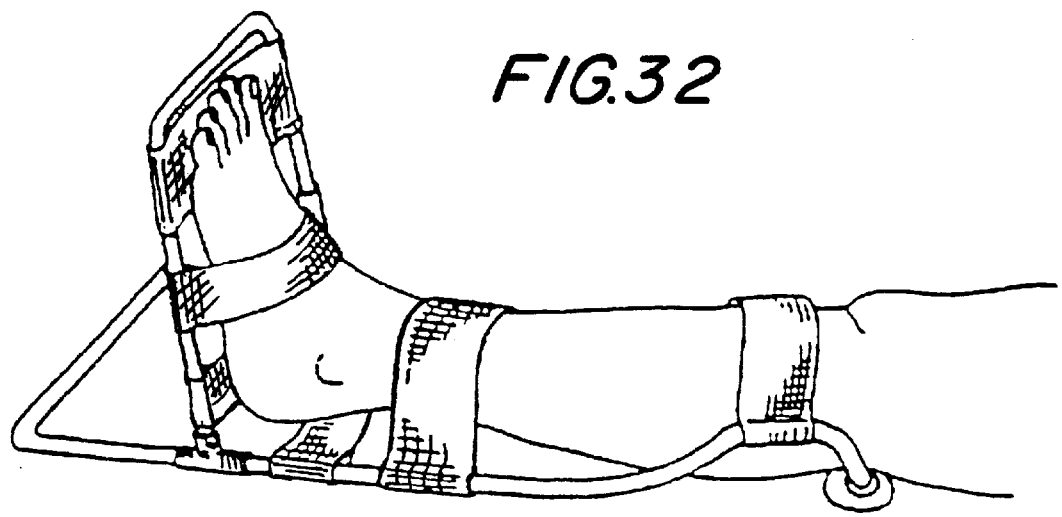
FIG. 32 shows an embodiment of the medical device according to the present invention configured as an orthopedic support for the lower leg and foot, for use in a resting position.
Figure 33:
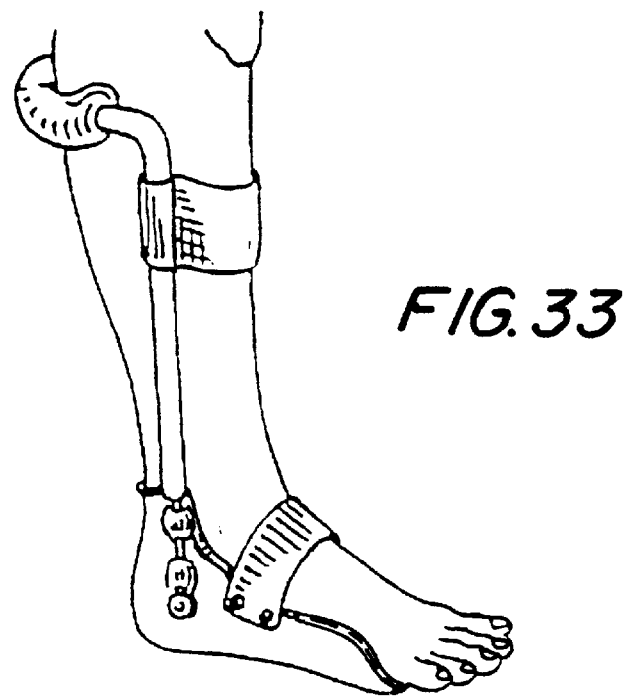
FIG. 33 shows an embodiment of the medical device according to the present invention configured as an orthopedic support for the lower leg and foot, for use in a vertical or walking position.

The respective implements shown in FIGS. 16a–o include:
a. hairbrush
b. shaving lather brush
c. shaving razor
d. toothbrush
e. spoon
f. fork
g. circular knife or cutting wheel ("pizza cutter" type cutting device)
h. vegetable peeler
i. sucking disk or aspiration device
j. chalk
k. eraser
l. magnet
m. artist's paint brush
n. buttoning device to assist in button closure
o. universal connecting device From the flexibility of the device object of the present invention, the professional can be in the position to mold it into the most adequate and functional position without need of any preliminary operation.

The multiflexible ergonomic therapeutic device of the present invention does not require the manufacture of molds in its pre-molded versions which slowly requires that it be placed on the affected limb or articulation and in some cases minor and quick adjustments are made.

The material employed and how it is going to be produced. The device of the present invention can be useful for hyorotherapy because it can also be sterilized.

The simple rod shaped device can be produced in different length and diameters according to its final use.

The doctor, therapist or orthopedic technician, employing the present device to make a trough, splint, collar or orthesis, merely needs the knowledge that is intrinsic to the pathology and corrective or preventive therapeutic procedures. Therefore, the usefulness found in the present device is its low cost, its versatility and the lack of any need for special expertise for its manufacture, which eliminates the waste in time of the former technologies and translates into greater benefits to the injured person.

Throughout the course of the pathology it proves to be quite economical, since with single orthesis all the needs are thereby covered.

In addition the present device shall be of great use in many urgent post-operative and emergency cases with regards to the immobilization of certain articulations and to mobilize others.

Therefore, the device of the present invention stands out from those of the previous technology, mainly because:

the support arches only overlap small areas of contact, thus avoiding pressures and chafing;

there is freedom of movement in the articulations adjacent to the immobilized places;

there is no loss of sensitivity, since most of the sensitive areas remain uncovered and free to move;

esthetically it preserves the natural appearance of the affected limb, since as we have emphasized it only covers small areas of the limb;

as to the patient's self-image, the patient is not inconvenienced or embarrassed by an unnatural shape of his hand when the splint is made with the present technology, consisting of a compounded product which fits perfectly with the anatomical lines of the injured limb;

due to its "transparency" one is in a position to follow up the rehabilitation and clinical development of the polytraumatized limb, without having to remove the splint, that is the follow up of the recrudescence of the tumid area and the return of sensation to the limb;

the range of its use is increased as a teaching tool in future immobilization during classes in orthopedics, surgery, physiotherapy, occupational therapy among others;

it is a recyclable, adjustable, flexible, fitting and refittable material;

it is employed as a pre-splint during which the function of the limb due to surgery, immobilization or positioning can be evaluated;

through periodic adjustment of the device the optimum settings of the device in serious cases of disabilities can be established over a certain period of time and the setting of the device further fine tuned in order to meet the comfort and convenience of the patient.

What is claimed is:

1. A multi-purpose medical device, that is alternatively configurable as an external orthopedic fixation device and a multi-functional prosthesis, for use alternatively to provide therapeutic support and/or traction for a sprained, fractured, or broken limb of a warm-blooded animal, and to provide at least one of substitute elementary limb functionality and substitute multi-purpose specific task functionality of a limb of a warm-blooded animal, the medical device comprising:

a.) at least one tubular elongate member, having a length, a first end, and an opposite, second end, the at least one tubular elongate member being made from a flexible material that is both capable of retaining a shape into which the tubular elongate member is configured, and capable of being reconfigured into an alternative shape, such that the at least one tubular elongate member is configurable by itself or in combination with other such tubular elongate members into a shape selected from the group consisting of: open, two-dimensionally closed, and three-dimensionally closed;

b.) at least one strengthening rod, having a length at least equal to the length of the at least one elongate member, a first end, and an opposite, second end, the strengthening rod being positioned inside the tubular elongate member, such that where there is a plurality of tubular elongate members, there is a corresponding strengthening rod associated with each tubular elongate member, the strengthening rod being made from a material that is simultaneously flexible, capable of being reconfigured from one shape to another, and capable of providing support and maintaining its shape until sufficient force is applied thereto to change its shape;

c.) at least one pair of end caps, with each end cap of the pair being attached to an end of a tubular elongate member at respective ends of the device, when the device is utilized in an open configuration;

d.) a plurality of different task-performing tools, each having a first end for attachment to an end of a tubular elongate member, and a second end having a different task-performing tool attached thereto for performing a specific task; and e.) where a single one or a plurality of tubular elongate members are utilized to form a closed structure, at least one connector to connect the ends of a single tubular elongate member to one another or to connect several tubular elongate members to one another.

2. A combined, reconfigurable, multi-purpose medical device, that is both an external orthopedic fixation device and a multi-functional prosthesis, for use alternatively to provide support and/or traction for a sprained, fractured, or broken limb of a warm-blooded animal, and to provide at least one of substitute elementary limb functionality and substitute multi-purpose specific task functionality of a limb of a warm-blooded animal, the medical device comprising:

a.) at least one elongate member, having a length, a first end, and an opposite, second end, the at least one elongate member having a tubular configuration with an outside diameter and a cross section, with the first and second ends of the at least one elongate member being open, the at least one elongate member being made from a flexible material that is both capable of retaining a shape into which the elongate member is configured, and capable of being reconfigured into an alternative shape, the length of the at least one elongate member being such that where the function of the medical device is as an artificial prosthesis, the length of the at least one elongate member, and, where a plurality of elongate members are present, a total length of all such individual elongate members, is sufficient to enable the at least one elongate member to be anchored to at least one anchoring limb or portion of a limb adjacent to the limb for which substitute function is to be provided, by wrapping a portion of the length of the at least one elongate member, proximate to at least one end thereof, around such at least one anchoring limb or portion thereof; and where the function of the medical device is to provide support and/or traction, the length of the at least one elongate member, and, where a plurality of elongate members are present, a total length of all such individual elongate members, is sufficient to provide a frame around the limb to be supported or for which traction is to be provided;

b.) at least one strengthening rod, having a length at least equal to the length of the at least one elongate member, and a first end, and an opposite, second end, the strengthening rod being positioned inside the elongate member, such that where there is a plurality of elongate members, there is a corresponding strengthening rod associated with each elongate member, the strengthening rod being made from a material that is simultaneously flexible, capable of being reconfigured from one shape to another, and capable of providing support and maintaining its shape until sufficient force is applied thereto to change its shape;

c.) at least one pair of end caps, with each end cap of the pair being attached to an and of an elongate member at a respective end of the device, the end caps providing closure to the open ends of the at least one elongate member and a cover to the ends of the at least one strengthening rod; and d.) where the device is to provide substitute multi-purpose specific task functionality of a limb, a plurality of different task-performing tools, each having a first end for attachment to an end of an elongate member in place of and end cap, and a second end having a different task-performing tool attached thereto for performing a specific task.

3. The medical device according to claim 2, further comprising:

d.) at least one cushioning support, having a length, a first end, and an opposite, second end, the cushioning support having a tubular configuration with an inside diameter and an outside diameter, such that the inside diameter of the cushioning support is greater than the outside diameter of the elongate member, and the first and second ends of the cushioning support are open, with the cushioning support being positioned over the elongate member along a section of the length thereof that is proximate to a limb or anatomical part that is to be cushioned against impact by or abrasion from the elongate member, the cushioning support being slidably movable along the length of the elongate member, and the cushioning support being made from a material that is soft and impact-absorbing; and e.) at least one stop, attached to the at least one cushioning support, such that where there is a plurality of cushioning supports, each such cushioning support has at least one stop attached thereto, the stop being for causing the cushioning support to remain fixed at a position along the length of the elongate member when the stop is actuated, and such that when the stop is deactuated, the cushioning support is repositionable to an alternative position along the length of the elongate member by application of sufficient force to slide the cushioning support along the length of the elongate member to such alternative position.

4. The medical device according to claim 3, further comprising a plurality of connectors spaced along the length of at least one elongate member, the connectors being for each receiving one end of a traction member, there being provided at least one such traction member, each traction member having a proximal end for attachment to a digital limb, and a distal end for attachment to a connector.

5. The medical device according to claim 3, further comprising at least one traction member, the traction member having a proximal end for attachment to a digital limb, and a distal end that is flexibly connected to an elongate member.

6. The medical device according to claim 5, wherein the proximal end of the traction member is attachable to a digital limb selected from the group consisting of a finger and a toe.

7. The medical device according to claim 5, wherein there are four traction members.

8. The medical device according to claim 5, wherein there are five traction members.

9. The medical device according to claim 3, wherein the at least one elongate member is made from a moldable material.

10. The medical device according to claim 9, wherein the moldable material is a plastic.

11. The medical device according to claim 3, wherein the at least one pair of end caps each has a proximal end at which they are attached to the ends of the device, the proximal ends of the end caps having a diameter that is greater than the outside diameter of the at least one elongate member, such that the end caps are attached to the ends of the device by being attached to the ends of the elongate member by sliding an end cap over each end of the elongate member.

12. The medical device according to claim 3, wherein the at least one pair of end caps each has a proximal end at which they are attached to the ends of the device, the proximal ends of the end caps having a diameter that is less than the outside diameter of the at least one elongate member, such that the end caps are attached to the ends of the device by being attached to the ends of the elongate member by sliding an end cap into each end of the elongate member.

13. The medical device according to claim 3, wherein the ends of the at least one strengthening rod are knurled.

14. The medical device according to claim 13, wherein the at least one strengthening rod has a length greater than the length of the at least one elongate member, such that each end of the at least one strengthening rod extends beyond the corresponding end of the at least one elongate member, and further that each end cap has a connector therein for connecting to one of the knurled ends of the strengthening rod, such that the end caps are attached to the knurled ends of the strengthening rod by the knurled ends of the strengthening rods exerting a pressure against the connectors in the end caps.

15. The medical device according to claim 3, wherein when the function of the device is (A.), specific substitute functional utility to perform common tasks is provided by replacing one of the end caps with an accessory having a first end for attachment to an end of the elongate member, and a second end having a task-performing tool attached thereto for performing a specific task.

16. The medical device according to claim 15, wherein the task-performing tool attached to the second end of the accessory is selected from the group consisting of: a hair comb; a hair brush; a shaving lather application brush; a shaving razor; a toothbrush; a knife; a spoon; a fork; a drinking straw; an aspiration device; a rotating blade cutting device; a peeling device; a writing implement; a piece of chalk; an eraser; a paint brush; a button-closing device; a magnet; and a universal-connecting device.

17. The medical device according to claim 3, wherein the warm-blooded animal is a vertebrate.

18. The medical device according to claim 3, wherein the warm-blooded animal is a human being.

19. The medical device according to claim 2, wherein the warm-blooded animal is a vertebrate.

20. The medical device according to claim 2, wherein the warm-blooded animal is a human being.

21. A multi-purpose medical device for providing at least one of the functions of:

A.) an artificial prosthesis for providing substitute function for at least one upper limb selected from the group consisting of a finger, a hand, a forearm, an elbow, and an upper arm of a human being, who has experienced a compromise of function of, or a complete loss of function of, such limb, through physical and/or neurological disease and/or damage, or who has experienced actual physical loss of all or part of such limb through traumatic accident and/or amputation, with concomitant loss of all or part of the corresponding neurological function of such limb; and B.) an external orthopedic fixation device for providing support and/or traction for a sprained, fractured, or broken limb selected from the group consisting of a finger, a hand, a forearm, an elbow, an upper arm, a toe, a foot, an ankle, a lower leg, a knee, an upper leg, a neck, and a back of a human being;

the medical device having a length, a first end, and an opposite, second end, and comprising;

a.) at least one elongate member, having a length, a first end, and an opposite, second end, the at least one elongate member having a tubular configuration with an outside diameter and a cross section, with the first and second ends of the at least one elongate member being open, the at least one elongate member being made from a flexible material that is both capable of retaining a shape into which the elongate member is configured, and capable of being reconfigured into an alternative shape, the length of the at least one elongate member being such that where the function of the medical device is (A.), the length of the at least one elongate member, and, where a plurality of elongate members are present, a total length of all such individual elongate members, is sufficient to enable the at least one elongate member to be anchored to at least one anchoring limb or portion of a limb adjacent to the limb for which substitute function is to be provided, by wrapping a portion of the length of the at least one elongate member, proximate to at least one end thereof, around such at least one anchoring limb or portion thereof; and where the function of the medical device is (B.), the length of the at least one elongate member, and, where a plurality of elongate members are present, a total length of all such individual elongate members,is sufficient to provide a frame around the limb to be supported or for which traction is to be provided;

b.) at least one strengthening rod, having a length at least equal to the length of the at least one elongate member, and a first end, and an opposite, second end, the strengthening rod being positioned inside the elongate member, such that where there is a plurality of elongate members, there is a corresponding strengthening rod associated with each elongate member, the strengthening rod being made from a material that is simultaneously flexible, capable of being reconfigured from one shape to another, and capable of providing support and maintaining its shape until sufficient force is applied thereto to change its shape;

c.) at least one pair of end caps, with each end cap of the pair being attached to a respective end of the device, the end caps providing closure to the open ends of the at least one elongate member and a cover to the ends of the at least one strengthening rod;

d.) at least one cushioning support, having a length, a first end, and an opposite, second end, the cushioning support having a tubular configuration with an inside diameter and an outside diameter, such that the inside diameter of the cushioning support is greater than the outside diameter of the elongate member, and the first and second ends of the cushioning support are open, with the cushioning support being positioned over the elongate member along a section of the length thereof that is proximate to a limb or anatomical part that is to be cushioned against impact by or abrasion from the elongate member, the cushioning support being slidably movable along the length of the elongate member, and the cushioning support being made from a material that is soft and impact-absorbing; and e.) at least one stop, attached to the at least one cushioning support, such that where there is a plurality of cushioning supports, each such cushioning support has at least one stop attached thereto, the stop being for causing the cushioning support to remain fixed at a position along the length of the elongate member when the stop is actuated, and such that when the stop is deactuated, the cushioning support is repositionable to an alternative position along the length of the elongate member by application of sufficient force to slide the cushioning support along the length of the elongate member to such alternative position.

22. The medical device according to claim 21, wherein the cross section of the elongate member in (a.) is circular.

23. The medical device according to claim 21, wherein there is a single elongate member.

24. The medical device according to claim 23, further comprising at least one rigid support member, such that the rigid support member has a shape and contour substantially identical to that of the limb to be supported, with the rigid support having at least one connector thereon to which the elongate member is attachable at or near at least one of the ends of the elongate member.

25. The medical device according to claim 24, wherein the rigid support further comprises at least one flexible strap, for securing the limb to the rigid support, the strap having a first end and a second end, the strap being detachably attached to the rigid support at least one end of the strap and fixedly or detachably attached to the rigid support at the other end of the strap.

26. The medical device according to claim 25, wherein the strap is made from a material selected from the group consisting of fabric, leather, plastic, and an elastic material.

27. The medical device according to claim 25, wherein the strap is detachably detached to the rigid support by at least one fastener.

28. The medical device according to claim 27, wherein the fastener is selected from the group consisting of: a button; a snapper; a zipper; a patch or a strip of adhesive tape; and a patch or a strip of Velcro™ type closure material, having a plurality of hooks on the surface of a first portion thereof and a plurality of loops on the surface of a second portion thereof, with which the first surface cooperates to effect a releasable closure between the surfaces.

29. The medical device according to claim 25, wherein the rigid support has the shape and contour of a hand.

30. The medical device according to claim 25, wherein the rigid support has the shape and contour of a foot.

31. The medical device according to claim 25, wherein there are two rigid supports.

32. The medical device according to claim 31, wherein the first rigid support has the shape and contour of an upper region of the back; and the second rigid support has the shape and contour of a lower region of the back.

33. The medical device according to claim 21, wherein there is a plurality of elongate members.

34. The medical device according to claim 33, wherein there are two elongate members.

35. The medical device according to claim 34, wherein when the function of the device is (B.), and the two elongate members are joined together to form a closed frame, having either a two-dimensional or a three-dimensional configuration, the frame being capable either of supporting or surrounding the limb for which support and/or traction is being provided, the medical device further comprises two linear, uni-dimensional joints, each having a length, a first end, and an opposite, second end, with the two elongate member s being joined together by the joints, such that one end of the first joint is attached to one end of the first elongate member; the other, opposite end of the first joint is attached to one end of the second elongate member; one end of the second joint is attached to the other, opposite end of the first elongate member; and the other, opposite end of the second joint is attached to the other, opposite end of the second elongate member.

36. The medical device according to claim 35, further comprising at least one panel of a flexible, soft webbing material, having a surface area, and first and second ends, the panel being attached at its first end to one elongate member at one point along the length thereof, and at its second end to the same or the other elongate member at another, opposite point along the total length thereof, such that the panel spans a section of the frame, in order to support and immobilize a limb.

37. The medical device according to claim 35, wherein outer surfaces of the uni-dimensional joints are covered with a cushioning material.

38. The medical device according to claim 33, wherein there are three elongate members.

39. The medical device according to claim 38, wherein when the function of the device is (B.), and the three elongate members are joined together to form a closed frame, having a three-dimensional configuration, with at least two of the elongate members lying in different planes, the frame being capable either of supporting or surrounding the limb for which support and/or traction is being provided, the medical device further comprises two non-linear, two-dimensional joints, each joint having a first linear section having a length, a first end, and an opposite, second end; and a second linear section, attached at a first end of the second linear section to the first linear section at a center point of the first linear section, forming an angle between the first and second linear sections, the second linear section also having a length and a second end opposite to the first end attached to the first linear section, such that two elongate members are attached to one another at opposing pairs of respective ends thereof by the first and second ends of the first linear sections of the two joints, and the third elongate member is attached to the first two elongate members by the second ends of the second linear sections of the two joints, thereby forming a three-dimensional frame structure having elongate members lying in at least two planes.

40. The medical device according to claim 39, wherein the angle formed between the first and second linear sections of the two-dimensional joint at the point of attachment of the two sections is a 90° right angle, such that the second linear section of the two-dimensional joint is perpendicularly attached to the first linear section of the two-dimensional joint, forming a "T" therewith.

41. The medical device according to claim 39, wherein the angle formed between the first and second linear sections of the two-dimensional joint at the point of attachment of the two sections is a non-right angle.

42. The medical device according to claim 41, wherein the non-right angle is an acute angle.

43. The medical device according to claim 39, wherein two elongate members lie in a first plane, and the third elongate member lies in a second plane perpendicular to the first plane.

44. The medical device according to claim 39, further comprising at least one panel of a flexible, soft webbing material, having a surface area, and first and second ends, the panel being attache d at its first end to on e elongate member at one point along the length thereof, and at its second end to the same or another elongate member at another, opposite point along the total length thereof, such that the panel spans a section of the frame, in order to support and immobilize a limb.

45. The medical device according to claim 39, wherein outer surfaces of the two-dimensional joints are covered with a cushioning material.

46. The medical device according to claim 21, wherein when the function of the device is (B.), the device further comprises a linear, uni-dimensional joint, having a length, a first end, and an opposite, second end, such that the elongate member is configured into a closed frame capable either of supporting or surrounding the limb for which support and/or traction is being provided, the closed frame being formed by a plurality of angular and/or arcuate bends in the elongate member, the bends having a total equivalent internal angular measurement of 360°, with the pair of end caps being removed so that the first and second ends of the elongate member are connected together by the uni-dimensional joint, with one end of the elongate member being attached to one end of the joint, and the other, opposite end of the elongate member being attached to the other, opposite end of the joint.

47. The medical device according to claim 46, wherein the closed frame, into which the elongate member is configured, is two-dimensional, such that segments of the elongate member incorporating angular and/or arcuate bends therein all lie within a single planar surface.

48. The medical device according to claim 46, wherein the closed frame, into which the elongate member is configured, is three-dimensional, such that segments of the elongate member incorporating angular and/or arcuate bends therein do not all lie within a single planar surface.

49. The medical device according to claim 46, further comprising at least one panel of a flexible, soft webbing material, having a surface area, and first and second ends, the panel being attached at its first end to the elongate member at one point along the length thereof, and at its second end to the elongate member at another, opposite point along the length thereof, such that the panel spans a section of the frame, in order to support and immobilize a limb.

50. The medical device according to claim 46, wherein an outer surface of the uni-dimensional joint is covered with a cushioning material.

51. A multi-purpose medical device for providing at least one of the functions of:
   A.) an external orthopedic fixation device for providing support and/or traction for a sprained, fractured, or broken limb selected from the group consisting of a finger, a hand, a forearm, an elbow, an upper arm, a toe, a foot, an ankle, a lower leg, a knee, an upper leg, a neck, and a back of a human being; and
   B.) an artificial prosthesis for providing substitute function for at least one upper limb selected from the group consisting of a finger, a hand, a forearm, an elbow, and an upper arm of a human being, who has experienced a compromise of function of, or a complete loss of function of, such limb, through physical and/or neurological disease and/or damage, or who has experienced actual physical loss of all or part of such limb through traumatic accident and/or amputation, with concomitant loss of all or part of the corresponding neurological function of such limb;
   the medical device having a length, a first end, an opposite, second end, and comprising:
      a.) at least one elongate member, having a length, a first end, and an opposite, second end, the at least one elongate member having a tubular configuration with an outside diameter and a cross section, with the first and second ends of the at least one elongate member being open, the at least one elongate member being made from a flexible material that is both capable of retaining a shape into which the elongate member is configured, and capable of being reconfigured into an alternative shape, the length of the at least one elongate member being such that
         where the function of the medical device is (A.), the length of the at least one elongate member, and, where a plurality of elongate members are present, a total length of all such individual elongate members, is sufficient to provide a frame around the limb to be supported or for which traction is to be provided; and
         where the function of the medical device is (B.), the length of the at least one elongate member, and, where a plurality of elongate members are present, a total length of all such individual elongate members, is sufficient to enable the at least one elongate member to be anchored to at least one anchoring limb or portion of a limb adjacent to the limb for which substitute function is to be provided, by wrapping a portion of the length of the at least one elongate member, proximate to at least one end thereof, around such at least one anchoring limb or portion thereof;
      b.) at least one strengthening rod, having a length at least equal to the length of the at least one elongate member, and a first end, and an opposite, second end, the strengthening rod being positioned inside the elongate member, such that where there is a plurality of elongate members, there is a corresponding strengthening rod associated with each elongate member, the strengthening rod being made from a material that is simultaneously flexible, capable of being reconfigured from one shape to another, and capable of providing support and maintaining its shape until sufficient force is applied thereto to change its shape;
      c.) at least one cushioning support, having a length, a first end, and an opposite, second end, the cushioning support having a tubular configuration with an inside diameter and an outside diameter, such that the inside diameter of the cushioning support is greater than the outside diameter of the elongate member, and the first and second ends of the cushioning support are open, with the cushioning support being positioned over the elongate member along a section of the length thereof that is proximate to a limb or anatomical part that is to be cushioned against impact by or abrasion from the elongate member, the cushioning support being slidably movable along the length of the elongate member, and the cushioning support being made from a material that is soft and impact-absorbing;
      d.) at least one stop, attached to the at least one cushioning support, such that where there is a plurality of cushioning supports, each such cushioning support has at least one stop attached thereto, the stop being for causing the cushioning support to remain fixed at a position along the length of the elongate member when the stop is actuated, and such that when the stop is deactuated, the cushioning support is repositionable to an alternative position along the length of the elongate member by application of sufficient force to slide the cushioning support along the length of the elongate member to such alternative position; and
      e.) at least one pair of end caps, with each end cap of the pair being attached to a respective end of the device, the end caps providing closure to the open ends of the at least one elongate member and a cover to the ends of the at least one strengthening rod.

52. A method for alternatively providing therapeutic and rehabilitative treatment to a person, the treatment being selected from the following group (A) and (B),
   (A.) external orthopedic fixation to an injured limb; and
   (B.) at least one of substitute basic limb functionality and substitute limb-specific task-performing capability, for an incapacitated or missing limb;
   the method comprising:
      a.) selecting an application (A) or (B);
      b.) providing a multi-purpose medical device, that is alternatively configurable as an external orthopedic fixation device for application (A), and as a multi-functional prosthesis for application (B), the device including:
         i.) at least one tubular elongate member, having a length, a first end, and an opposite, second end, the at least one tubular elongate member being made from a flexible material that is both capable of retaining a shape into which the tubular elongate member is configured, and capable of being reconfigured into an alternative shape, such that the at least one tubular elongate member is configurable by itself or in combination with other such tubular elongate members into a shape selected from the group consisting of: open, two-dimensionally dimensionally closed, and three-dimensionally closed;

ii.) at least one strengthening rod, having a length at least equal to the length of the at least one elongate member, a first end, and an opposite, second end, the strengthening rod being positioned inside the tubular elongate member, such that where there is a plurality of tubular elongate members, there is a corresponding strengthening rod associated with each tubular elongate member, the strengthening rod being made from a material that is simultaneously flexible, capable of being reconfigured from one shape to another, and capable of providing support and maintaining its shape until sufficient force is applied thereto to change its shape;

iii.) at least one pair of end caps, with each end cap of the pair being attached to an end of a tubular elongate member at respective ends of the device, when the device is utilized in an open configuration;

iv.) a plurality of different task-performing tools, each having a first end for attachment to an end of a tubular elongate member, and a second end having a different task-performing tool attached thereto for performing a specific task; and v.) where a single one or a plurality of tubular elongate members are utilized to form a closed structure, at least one connector to connect the ends of a single tubular elongate member to one another or to connect several tubular elongate members to one another; and c.) alternatively performing one of the steps (c.1), (c.2), and (c.3), selected from the following group:

c.1.) forming the device into an open or closed external orthopedic fixation device for supporting, immobilizing, and/or surrounding an injured limb;

c.2.) fitting the device to a user so as to provide substitute basic limb functionality for a limb selected from the group consisting of a finger, a hand, a forearm, an elbow, an upper arm, a toe, a foot, an ankle, a lower leg, a knee, and an upper leg; and c.3.) fitting the device to a user so as to provide substitute specific task-performing functionality for a task function requiring the use of fingers and/or a hand, with the device having a tool according to (b.)(iv.) for the performance of a specific task attached to at least one end thereof.

53. A method for alternatively providing:

(A.) external orthopedic fixation to an injured limb, and (B) providing substitute functionality for an incapacitated limb, the method comprising:

a.) selecting an application (A) or (B);

b.) providing a medical device appropriate for performing the selected application, the medical device at least having a length, a first end, an opposite, second end, and including:

i.) at least one elongate member, having a length, a first end, and an opposite, second end, the at least one elongate member having a tubular configuration with an outside diameter and a cross section, with the first and second ends of the at least one elongate member being open, the at least one elongate member being made from a flexible material that is both capable of retaining a shape into which the elongate member is configured, and capable of being reconfigured into an alternative shape, the length of the at least one elongate member being such that where the function of the medical device is as an external orthopedic fixation device, the length of the at least one elongate member, and, where a plurality of elongate members are present, a total length of all such individual elongate members, is sufficient to provide a frame around the limb to be supported or for which traction is to be provided; and where the function of the medical device is as an artificial prosthesis, the length of the at least one elongate member, and, where a plurality of elongate members are present, a total length of all such individual elongate members, is sufficient to enable the at least one elongate member to be anchored to at least one anchoring limb or portion of a limb adjacent to the limb for which substitute function is to be provided, by wrapping a portion of the length of the at least one elongate member, proximate to at least one end thereof, around such at least one anchoring limb or portion thereof;

ii.) at least one strengthening rod, having a length at least equal to the length of the at least one elongate member, and a first end, and an opposite, second end, the strengthening rod being positioned inside the elongate member, such that where there is a plurality of elongate members, there is a corresponding strengthening rod associated with each elongate member, the strengthening rod being made from a material that is simultaneously flexible, capable of being reconfigured from one shape to another, and capable of providing support and maintaining its shape until sufficient force is applied thereto to change its shape;

iii.) at least one cushioning support, having a length, a first end, and an opposite, second end, the cushioning support having a tubular configuration with an inside diameter and an outside diameter, such that the inside diameter of the cushioning support is greater than the outside diameter of the elongate member, and the first and second ends of the cushioning support are open, with the cushioning support being positioned over the elongate member along a section of the length thereof that is proximate to a limb or anatomical part that is to be cushioned against impact by or abrasion from the elongate member, the cushioning support being slidably movable along the length of the elongate member, and the cushioning support being made from a material that is soft and impact-absorbing;

iv.) at least one stop, attached to the at least one cushioning support, such that where there is a plurality of cushioning supports, each such cushioning support has at least one stop attached thereto, the stop being for causing the cushioning support to remain fixed at a position along the length of the elongate member when the stop is actuated, and such that when the stop is deactuated, the cushioning support is repositionable to an alternative position along the length of the elongate member by application of sufficient force to slide the cushioning support along the length of the elongate member to such alternative position; and v.) at least one pair of end caps, with each end cap of the pair being attached to a respective end of the device, the end caps providing closure to the open ends of the at least one elongate member and a cover to the ends of the at least one strengthening rod; and c.) further providing one or more additional elements of the medical device, selected from the following group (vi)–(viii), depending on the selected application:

vi.) at least one linear, uni-dimensional joint, having a length, a first end, and an opposite, second end, for enabling the elongate member to be configured into a closed frame capable either of supporting or surrounding the limb for which support and/or traction is being provided, the closed frame being formed by a plurality of angular and/or arcuate bends in the elongate member, the bends having a total equivalent internal angular measurement of 360°, with the pair of end caps being removed so that the first and second ends of the elongate member are connected together by the uni-dimensional joint, with one end of the elongate member being attached to one end of the joint, and the other, opposite end of the elongate member being attached to the other, opposite end of the joint;

vii.) at least one pair of non-linear, two-dimensional joints, each two-dimensional joint having a first linear section having a length, a first end, and an opposite, second end; and a second linear section, attached at a first end of the second linear section to the first linear section at a center point of the first linear section, forming an angle between the first and second linear sections, the second linear section also having a length and a second end opposite to the first end attached to the first linear section, such that two elongate members are attached to one another at opposing pairs of respective ends thereof by the first and second ends of the first linear sections of the two joints, and the third elongate member is attached to the first two elongate members by the second ends of the second linear sections of the two joints, thereby forming a three-dimensional frame structure having elongate members lying in at least two planes;

viii.) a plurality of accessories capable of being attached to either end of an elongate member in place of at least one of the end caps, each accessory having a first end for attachment to an end of the elongate member, and a second end having a task-performing tool attached thereto for performing a specific task, the task-performing tool being selected from the group consisting of: a hair comb; a hair brush; a shaving lather application brush; a shaving razor; a toothbrush; a knife; a spoon; a fork; a drinking straw; an aspiration device; a rotating blade cutting device; a peeling device; a writing implement; a piece of chalk; an eraser; a paint brush; a button-closing device; a magnet; and a universal-connecting device; and d.) where application (A) has been selected, using the medical device as an external orthopedic fixation device for providing support and/or traction for a sprained, fractured, or broken limb selected from the group consisting of a finger, a hand, a forearm, an elbow, an upper arm, a toe, a foot, an ankle, a lower leg, a knee, an upper leg, a neck, and a back of a human being, by configuring the device to alternatively form a structure selected from the following group (d)(i)–(d)(iii):

i.) a closed frame formed form a single elongate member, the closed frame being capable either of supporting or surrounding the limb for which support and/or traction is being provided, the closed frame being formed by a plurality of angular and/or arcuate bends in the elongate member, the bends having a total equivalent internal angular measurement of 360°, with the pair of end caps being removed so that the first and second ends of the elongate member are connected together by a uni-dimensional joint, with one end of the elongate member being attached to one end of the joint, and the other, opposite end of the elongate member being attached to the other, opposite end of the joint, and further such that the closed frame is alternatively:

two-dimensional, such that segments of the elongate member incorporating angular and/or arcuate bends therein all lie within a single planar surface; or three-dimensional, such that segments of the elongate member incorporating angular and/or arcuate bends therein do not all lie within a single planar surface;

ii.) a closed frame formed from two elongate members that are joined together, the closed frame, having either a two-dimensional or a three-dimensional configuration, the closed frame being capable either of supporting or surrounding the limb for which support and/or traction is being provided, the closed frame being formed using two linear, uni-dimensional joints, with the two elongate members being joined together by the uni-dimensional joints, such that one end of the first joint is attached to one end of the first elongate member; the other, opposite end of the first joint is attached to one end of the second elongate member; one end of the second joint is attached to the other, opposite end of the first elongate member; and the other, opposite end of the second joint is attached to the other, opposite end of the second elongate member;

iii.) a closed frame formed from three elongate members that are joined together, the closed frame having a three-dimensional configuration, with at least two of the elongate members lying in different planes, the closed frame being capable either of supporting or surrounding the limb for which support and/or traction is being provided, the closed frame being formed using two non-linear, two-dimensional joints, such that two elongate members are attached to one another at opposing pairs of respective ends thereof by the first and second ends of the first linear sections of the two joints, and the third elongate member is attached to the first two elongate members by the second ends of the second linear sections of the two joints, thereby forming a three-dimensional frame structure having elongate members lying in at least two planes; and e.) where application (B) has been selected, using the medical device as an artificial prosthesis for providing substitute function for at least one upper limb selected from the group consisting of a finger, a hand, a forearm, an elbow, and an upper arm of a human being, who has experienced a compromise of function of, or a complete loss of function of, such limb, through physical and/or neurological disease and/or damage, or who has experienced actual physical loss of all or part of such limb through traumatic accident and/or amputation, with concomitant loss of all or part of the corresponding neurological function of such limb, by fitting the device to a user to provide at least one substitute limb functionality selected from the following group (e)(i)–(e)(ii):

i.) substitute basic limb functionality for a limb selected from the group consisting of a finger, a hand, a forearm, an elbow, an upper arm, a toe, a foot, an ankle, a lower leg, a knee, and an upper leg; and ii.) substitute specific task-performing functionality for a task function requiring the use of fingers and/or a hand, with the medical device having a tool according to (c.)(viii.) for the performance of a specific task selected therefrom, attached to at least one end of the medical device.

* * * * *